(12) United States Patent
Horvath

(10) Patent No.: US 11,275,077 B2
(45) Date of Patent: Mar. 15, 2022

(54) OLFACTORY DETECTOR FOR EARLY DIAGNOSIS OF OVARIAN CANCER

(71) Applicant: VOC DIAGNOSTICS AB, Ingaro (SE)

(72) Inventor: Gyorgy Horvath, Ingaro (SE)

(73) Assignee: VOC DIAGNOSTICS, Ingaro (SE)

( * ) Notice: Subject to any disclaimer, the term of this patent is extended or adjusted under 35 U.S.C. 154(b) by 326 days.

(21) Appl. No.: 16/313,465

(22) PCT Filed: Jun. 26, 2017

(86) PCT No.: PCT/SE2017/000029
§ 371 (c)(1),
(2) Date: Dec. 27, 2018

(87) PCT Pub. No.: WO2018/004414
PCT Pub. Date: Jan. 4, 2018

(65) Prior Publication Data
US 2019/0317073 A1    Oct. 17, 2019

(30) Foreign Application Priority Data
Jun. 27, 2016  (SE) .................................. 1630165-7

(51) Int. Cl.
*G01N 33/497*   (2006.01)
*G01N 1/24*   (2006.01)
(Continued)

(52) U.S. Cl.
CPC ............. *G01N 33/497* (2013.01); *G01N 1/24* (2013.01); *G01N 1/40* (2013.01); *G01N 33/0031* (2013.01);
(Continued)

(58) Field of Classification Search
CPC .......... G01N 33/497; G01N 1/24; G01N 1/40; G01N 33/0031; G01N 33/0036;
(Continued)

(56) References Cited

U.S. PATENT DOCUMENTS

2002/0178789 A1* 12/2002 Sunshine ........... G01N 33/0009
73/31.06
2013/0150261 A1* 6/2013 Haick .................. G01N 33/497
506/12
2016/0334398 A1* 11/2016 Weissleder ............. B82Y 15/00

FOREIGN PATENT DOCUMENTS

CN         103454335 A  * 12/2013

* cited by examiner

*Primary Examiner* — Jennifer Wecker
*Assistant Examiner* — Oyeleye Alexander Alabi
(74) *Attorney, Agent, or Firm* — Flener IP & Business Law; Zareefa B. Flener

(57) ABSTRACT

The invention relates to a device and a method for cancer detection and screening, based on analysis of Volatile Organic Compounds emitted by certain cancerous tumors. The device and method provide high sensitivity and specificity analyses. The sample to be analysed may be e.g. blood or blood plasma. In one aspect, the invention is directed towards detection of or screening for gynaecological cancers, e.g. ovarian cancer. Particularly, the device comprises the following parts: a sample holder for a fluid or solid body sample; an air inlet; a detector tube comprising 4×4-16×4 sensors; optionally an individual potentiometer connected to each sensor of the detector tube; an analogue to digital signal converter; four control cards; a computer-based program for the registration and statistical calculation of results; and an electricity source.

14 Claims, 2 Drawing Sheets

Figure 1:
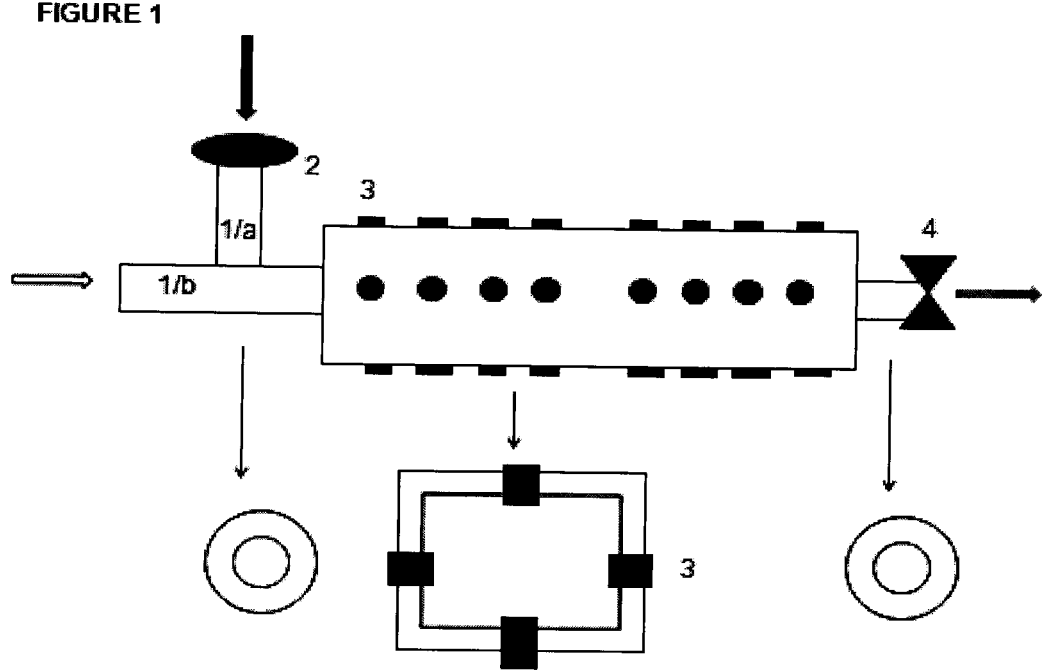

(51) Int. Cl.
*G01N 1/40* (2006.01)
*G01N 33/00* (2006.01)
*A61B 5/08* (2006.01)
*G01N 33/574* (2006.01)
*G01N 1/22* (2006.01)

(52) U.S. Cl.
CPC .......... *A61B 5/082* (2013.01); *G01N 33/0036* (2013.01); *G01N 33/57449* (2013.01); *G01N 2001/2229* (2013.01); *G01N 2001/245* (2013.01); *G01N 2033/4975* (2013.01)

(58) Field of Classification Search
CPC ..... G01N 33/57449; G01N 2001/2229; G01N 2001/245; G01N 2033/4975; A61B 5/082
See application file for complete search history.

OLFACTORY DETECTOR FOR EARLY DIAGNOSIS OF OVARIAN CANCER

TECHNICAL FIELD

The present invention relates to a device and method for cancer detection and diagnosis, and in particular to such device and method for ovarian cancer detection and diagnosis. Moreover, the invention provides efficient cancer screening possibilities.

BACKGROUND

Most cancers can be fatal if detected late. Cancers develop relatively slowly. From the first cancer cell in the body until first symptoms, and clinical diagnosis, usually several years elapse. Cancer diagnosed in the early stages has a much better chance of being cured. For this reason, screening was introduced for several known forms of cancers. The methods available may not always be reliable, whereby only a few screening programs have been set up.

When it comes to gynecological cancers, cervical screening contributes to early diagnosis of cervical cancer and is working well and uterine and vulvar cancers produce symptoms early on. Only for ovarian cancer would there be a need for general screening.

Ovarian cancer is the eighth most common cancer among women worldwide. In Sweden alone, ovarian cancer represents an annual incidence of just under 800 cases. Early discovered (ca. 30% of newly diagnosed ovarian cancers) belong to clinical stages I-II. Patients with such early discovered cancers have relatively good survival prospects. In contrast, about 70% of all newly diagnosed cases belong to stage which means that the survival rate for the patients is low. The overall five-year survival rate is just below 50% (47-48% in Sweden). The latter fact means that more than 400 women die annually from ovarian cancer in Sweden alone.

The survival rate for ovarian cancer patients during the last 10 years has not been improved at all. Biggest problem is the lack of a reliable screening method for early diagnosis. The known and used diagnostic methods such as ultrasound, X-ray, CA-125 analysis (as a tumor marker) all have too low sensitivity and specificity to be used for mass-screening, Due to the high mortality rates of ovarian cancer the disease is highly suitable for screening of healthy populations. A method with sufficient sensitivity and specificity could save hundreds of lives each year in Sweden alone.

The discovery of the specific Volatile Organic Compounds (VOCs) emitted by various cancerous tumors resulted in trials with trained dogs (1), and later with "electronic noses", to evaluate said dogs and electronic noses as possible diagnostic methods for different cancers. The present inventor demonstrated in several studies that also ovarian cancer cells emit specific VOCs (3). These VOCs can be detected in the patient's blood plasma (4, 5).

The development of so-called nano sensors could possibly be used for the diagnosis of lung cancer through analysis of exhaled air (2). Most substance found in circulating blood can be found also in the breath, albeit in lower concentrations. However, an analysis of exhaled air may be disturbed by various undiagnosed chemical reactions of the oral cavity or pharynx, and/or external agents such as environmental agents and cosmetic preparations.

Small tissue samples were examined by the inventor using a traditional "electronic nose", based on four TGS sensors. The results showed only very weak signals (6). Consequently, the method using traditional electronic noses is not useful in practice for early diagnosis and screening. That is because the sensitivity of these traditionally built electronic noses in the context of cancer diagnosis is very low. As an example, these noses may not detect VOCs from plasma or blood. Hence, there is a need for improved devices and methods for cancer diagnosis based on VOCs.

SHORT DESCRIPTION OF THE FIGURES

FIG. 1 shows a schematic representation of the "olfactory detector" according to the invention. The calculated volume of the detector tube is in one embodiment 361.0 $cm^3$. The inlet manifold with odor filter is marked by 1/a, while the location of the sample holder and air inlet during the "sensor recovery time" is marked with 1/b. The diameter, length and volume of the two air inlets may be the same. Air filter (2), sensors (3) and the fan (4) are in place. The rear tube fitted with a fan may have the same diameter, length and volume as each of the two air inlets.

Figure 2:
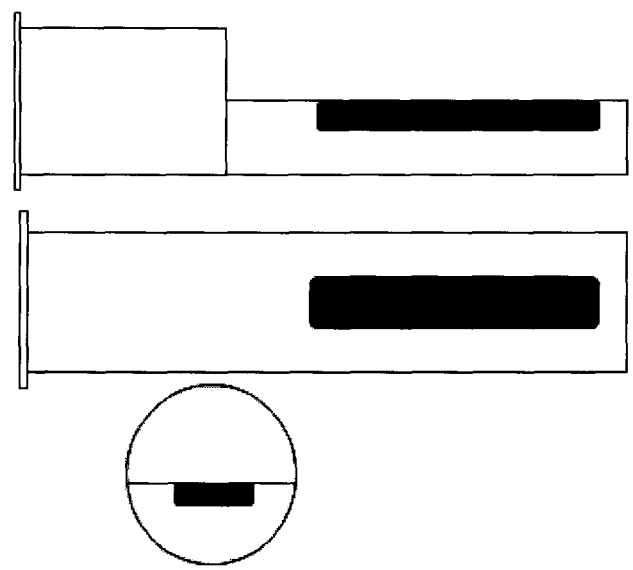

FIG. 2 shows the sample holder, with room for e.g. blood plasma, with a plasma surface area of 6.6 $cm^2$.

SHORT DESCRIPTION OF THE INVENTION

The invention relates to a device and a method for cancer detection and screening, based on analysis of Volatile Organic Compounds emitted by certain cancerous cells. The device and method provide high sensitivity and specificity analyses. The sample to be analysed may be e.g. blood or blood plasma. In one aspect, the invention is directed towards detection of or screening for gynaecological cancers, e.g. ovarian cancer. Particularly, the device comprises the following parts:

a sample holder for a fluid or solid body sample; an air inlet with a horizontal and a vertical shaft, wherein the diameter, length and volume of the two shafts may be the same;

an air filter fitted in the shaft not intended for sample holder insertion;

optionally a rear tube fitted with a fan, which tube may have the same diameter, length and volume as each of the two shafts;

a detector tube, said detector tube comprising 4×4-16×4 sensors, whereby the sensors comprise or consist of metal oxide sensors, all in quadruplicate, each sensor having adjustable heating voltage and adjustable circuit voltage, and each with set sensor resistance interval, for detecting volatile organic compounds from a sample;

optionally an individual potentiometer and load resistor with individually calculated resistance, respectively, connected to each sensor of the detector tube;

an analogue to digital signal converter connected to each sensor;

a computer-based analysis program operably connected to each individual sensor of the detector tube, through the analog to digital signal converter, for registration of signals and analysis of results;

and an electricity source.

DETAILED DESCRIPTION OF THE INVENTION

The present invention provides a device for early cancer diagnosis or screening, e.g. for gynecological cancers, lung cancer, breast cancer, cancer of the urinary tract, prostate cancer, head and neck cancer. In one aspect, the cancer to be diagnosed or screened for is ovarian cancer.

The device comprises the following parts:

a sample holder for a fluid or solid body sample;

an air inlet with a horizontal and a vertical shaft, wherein each shaft may have the same volume;

an air filter fitted in the shaft not intended for sample holder insertion;

optionally a rear tube fitted with a fan, which tube may have the same diameter, length and volume as each of the two shafts;

a detector tube, said detector tube comprising 4×4-16×4 sensors, whereby the sensors comprise or consist of metal oxide sensors, all in quadruplicate, each sensor having adjustable heating voltage, and adjustable circuit voltage, and each with set sensor resistance interval, for detecting volatile organic compounds from a sample;

optionally an individual potentiometer connected to each sensor of the detector tube;

a load resistor with individually calculated resistance connected to each sensor;

an analogue to digital signal converter connected to each sensor through control cards;

four control cards may be used of which each card is on the one side connected to each sensor on the same side of the detector tube, and on the other side the cards are connected to the analogue to digital converter, whereby these cards may work by individual potentiometers and load resistors, and have other resistors and amplifiers mounted on the cards;

a computer-based program which is used for the registration and statistical calculation of results, said computer being operably connected to each individual sensor of the detector tube, through the analog to digital signal converter and control cards.

The metal oxide sensors may in accordance with the invention be $SnO_2$ sensors.

The sample holder may be inserted horizontally or vertically through either of the shafts, and may have different shapes. It may have a round, oval or rectangular circumference. The sample holder has a cavity, wherein the sample is placed. The sample to be placed in the sample holder may be a body fluid, e.g. blood, blood plasma cyst fluid or urine, or a solid sample, e.g. a biopsy or a piece of a solid tumor. The sample holder may have a cavity with a surface of 6.6 $cm^2$. The detector tube may have a volume of 361.0 $cm^3$. In one embodiment, the sample holder has a cavity with a surface of 6.6 $cm^2$, and the detector tube has a volume of 361.0 $cm^3$.

The size of the cavity of the sample holder is correlated to the air flow through the device, i.e. the detector tube dimensions, so that the VOCs may reach the detector tube in an efficient fashion. VOCs need to be accumulated in the detector tube in high enough concentration, for the invention to work. To further improve evaporation of VOCs, heating of the sample holder may be made use of. Another possibility is the use of a fan to draw VOCs from the sample in the sample holder into the detector tube. The fan speed may need to be adjusted depending on the air filter used in the air inlet. Heating of the sample holder may also be combined with the use of a fan.

The air inlet may be single (as defined by a horizontal and vertical shaft in combination), or alternatively several air inlets may be made use of, to facilitate an efficient analysis process. At least one inlet (i.e. the horizontal or vertical shaft) is provided with an air filter, to ensure that the VOCs to be analyzed do indeed emanate from the sample. The air filter(s) may be simple activated coal filters. The person skilled in the art is well equipped to find and choose adequate air filter(s).

The detector tube may have various cross section geometries. Even though the term tube is used throughout herein for the sake of clarity, circular, elliptical or rectangular cross sections are all contemplated. The detector tube is advantageously made of a material minimizing turbulence in the tube. This is especially important if a fan is provided in the device. The detector tube may be made of stainless steel, and/or have an inner surface coated with e.g. Teflon.

The detector tube comprises 4×4-16×4 sensors mounted through the detector tube wall, with the sensing element facing inwards, towards the tube lumen. The number of sensors, and the individual sensor types, depends on the type of cancer to be detected.

In one aspect, the number of sensors is 4×4-12×4. In another aspect, the number of sensors is 4×4-8×4 sensors.

The designation "4×4" above should be construed as 4 sensors being placed on each side of a rectangular cross section of the tube, along the length of the tube. 16×4 should similarly be construed as meaning 16 sensors placed on each side of a rectangular cross section of the tube. If a circular cross section is used, the sensors would advantageously be evenly distributed throughout the circumference and length of the tube. "4×4" should also be construed as meaning that 4 types of sensors are present in quadruplicate, whereby the voltage used through each individual sensor of a quadruplicate is advantageously different. However, it is very important that the sensors of the same type are calibrated to different heating voltage within the above range, so that the program can distinguish signals coming from different VOCs.

The output signal from the sensors is converted to a digital signal by a signal converter. Said signal converter may be connected to each sensor, through circuit cards. Circuit cards advantageously have integrated protection for over voltage. The optional individual potentiometers, the load resistors for each individual sensor and amplifiers may be mounted on the circuit card.

In one embodiment, a Measurement card by National Instruments, USB 6218 is used as analogue to digital signal converter. Its 32 inputs, 16 bit may be connected to each sensor separately via the circuit voltage. The digital signal may be fed into a computer via a USB connection.

An amplifier may be connected to one or more of the sensors. Amplifiers are used to amplify signals and ensures that the signal strength does not drop through wires that connect different parts of the apparatus.

The sensing material in TGS gas sensors is metal oxide, most typically $SnO_2$. When a metal oxide crystal such as $SnO_2$ is heated at a certain high temperature in air, oxygen is adsorbed on the crystal surface with a negative charge. Then donor electrons in the crystal surface are transferred to the adsorbed oxygen, resulting in leaving positive charges in a space charge layer. Thus, surface potential is formed to serve as a potential barrier against electron flow. Inside the sensor, electric current flows through the conjunction parts (grain boundary) of $SnO_2$ micro crystals. At grain boundaries, adsorbed oxygen forms a potential barrier which prevents carriers from moving freely. The electrical resistance of the sensor is attributed to this potential barrier. In the presence of a deoxidizing gas, the surface density of the negatively charged oxygen decreases, so the barrier height in the grain boundary is reduced. The reduced barrier height decreases sensor resistance.

The sensors used may be metal oxide sensors, which are suitable for detecting VOCs. According to one aspect, the sensors are SnO2 sensors. These sensors can detect both aromatic and other hydrocarbons with good results.

The sensor requires two voltage inputs: heater voltage and circuit voltage. The heater voltage is applied to the integrated heater in order to maintain the sensing element at a specific temperature which is optimal for sensing. Circuit voltage is applied to allow measurement of voltage across a load resistor which is connected in series with the sensor. DC voltage is required for the circuit voltage since the sensor has a polarity.

According to the invention, a separate potentiometer may be connected to each sensor to enable individual selection of required temperature to maximize each sensor's sensitivity. As an alternative, the sensors may have a set potential. Circuit voltage is applied to allow measurement of voltage across a load resistor, which is connected in series with the sensor. Sensors' resistance to deoxidizing gas concentration (VOCs) is linear on a logarithmic scale within a range from several ppm to several thousand ppm.

A common power supply circuit can be used for both the circuit voltage and the heater voltage to fulfil the sensor's electrical requirements.

As regards the electricity source for the whole device as such (absent computer) a unit that converts 220V AC power to two separate outputs of between 3 and 15 V DC may be used.

The device according to the invention may consist of or comprise the sensors TGS 2602, TGS 2603, TGS 2620, and TGS 2600, all of which are present in quadruplicate. Use of these four Taguchi Gas Sensor (TGS) is the lowest number in a detector to detect ovarian cancer, in accordance with the invention.

The TGS 2602 has high sensitivity to low concentrations of odorous gases such as ammonia and H2S generated from waste materials. The sensor also has high sensitivity to low concentrations of VOCs such as toluene, an aromatic hydrocarbon.

The TGS 2603 has high sensitivity to low concentrations of odorous gases such as amine-series. E.g. trimethyl-amin, and sulphurous odors, such as methyl mercaptan. Both odors are present in human metabolism, and are often derived from dead cells.

The TGS 2620 has high sensitivity to the vapours of organic solvents as well as other volatile vapours such as hydrocarbons.

The TGS 2600 has high sensitivity to low concentrations of gaseous air contaminants such as hydrogen and carbon monoxide, methane and alcohol, occurring in human metabolism Alternatively, the device according to the invention may consists of or comprises the sensors TGS 2602, TGS 2603, TGS 2620, TGS 2611-E00, TGS 2600, and TGS 2444, all of which are present in quadruplicate. Completion of the above mentioned four sensors with TGS2611-E00 and TGS2444 improves the sensitivity of the device for the diagnosis of ovarian cancer.

TGS2611-E00 uses filter material in its housing which eliminates the influence of interference gases such as alcohol, resulting in highly selective response to methane gas. TGS 2444 displays good selectivity to ammonia. Both substances are present in low concentrations in cancerous tumors, usually originating from dead cells.

As yet an alternative, the device according to the invention may consists of or comprises the sensors TGS 2602, TGS 2603, TGS 2620, TGS 2611-E00, TGS 2600, TGS 2611-000, TGS 2444, and TGS 2610, all of which are present in quadruplicate. TGS2611-000 detects the hydrocarbons that TGS2611-EOO but their selectivity is different since it has no built-in filter materials, which facilitates differentiation between different VOCs. TGS2610 has high sensitivity for various hydrocarbons. With the addition of the two latter sensors, the device is capable of detecting VOCs not only from ovarian cancer but also from other gynecological cancers.

In accordance with the invention, the heating voltage to each sensor is regulated to between 2.5-5.5 V. Experiences from the inventor's investigations show that one can get the best signal quality for VOCs emitted from the plasma of ovarian cancer patients if the heating voltage is between said limits. However, it is necessary to fine-tune the voltage of each individual sensor to detect VOCs from ovarian and other gynecological cancers from blood plasma. (Table 4).

The correct selection of load resistance for each individual (or group of) sensor(s) enables the sensor to provide uniform characteristics.

In accordance with the invention there is provided a well-functioning system to use in the selection of load resistors. Calculation of the desired resistance is done by use of the formula: sensor resistance (in ohms) divided by resistance of the load resistor (in ohms) shall be=≤0.5. The method provided is used for the first time in this invention (Table 1). In the calculations for detection of ovarian cancer, the minimum values of the sensors' internal resistance have been used.

TABLE 1

| Sensors | Range of sensor resistance | Range of load resistance |
| --- | --- | --- |
| TGS 2602 | 10-100 kOhm | 20-200 kOhm |
| TGS 2603 | 20-200 kOhm | 40-400 kOhm |
| TGS 2620 | 1-5 kOhm | 2-10 kOhm |
| TGS 2611-E00 | 0.68-6.8 kOhm | 1.5-14 kOhm |
| TGS 2600 | 13.3-133 kOhm | 27-270 kOhm |
| TGS 2611 -C00 | 0.68-6.8 kOhm | 1.5-14 kOhm |
| TGS 2444 | 3.6-36.3 kOhm | 8-75 kOhm |
| TGS 2610 | 0.68-6.8 kOhm | 1.5-14 kOhm |

The device and method according to the invention is suitable for detecting aromatic hydrocarbons and/or amines.

The device and method according to the invention is suitable for detecting any of triethylamine, pyridine, toluene, p-xylene, E,Z-8,10-dodecadien-1-ol, trifluoromethylbenzene, hexadecanoic acid, docosane, 3-methylhexadecane, tetracosane, and heptadecane, as evidenced by comparative gas chromatography and mass spectrometry (GC-MS) studies. The above substances have been shown to be markers of cancer, e.g. gynaecological cancers.

The results of GC-MS studies showed significant differences, namely 10 out of 11 different compounds (VOCs) present in cancer cells "headspace" are either present only in minimal amounts, or not at all in control tissues. The exception is E,Z-8,10-dodecadien-1-ol, which is a pheromone that healthy tissues emit more of than cancer tissues. Whereas individual compounds of the above list have been shown to be markers of cancer, the panel disclosed has been shown to give an especially high statistical significance for ovarian cancer, as compared with control tissues.

In one embodiment of the invention, the set time for sample analysis is divided into 5 separate, subsequent parts, for improved statistical significance during statistical analysis. The breakdown into 5 separate, subsequent parts of the set time for sample analysis is based on the sensors' signal recording and sensors recovery time, i.e. rising and falling of the signal curve during the analysis. Calculating statistics in this way may further improve the sensitivity and specificity of the device. For statistical analysis, the set time for sample analysis is divided into separate parts. The number of separate parts may be 5. Five shorter intervals are preferably used to achieve more accurate calculation possibilities than analyzing the entire signal for 600 s.

Computer software is used for the statistical analyses. In Excel changes in the sensor circuit voltage may be registered, in volts, preferably ten times per second. The registrations may be 6000 individual values per sensor, for each analysis. These values are used in statistical calculations.

Upon completion of the statistical analysis a value between 0 and 1 may be obtained. Values above 0.5 indicate cancer.

The invention shall now be described with reference to a specific embodiment, which shall however not be seen as limiting the scope invention claimed in any way whatsoever.

Detailed Description of an Embodiment

The apparatus consists of 4 different parts.

A detector tube is provided as a stainless steel tube with a square cross section (FIG. 1). Eight holes are drilled on each side. The size of each hole corresponds to the sensor diameter, and a small rubber ring ensures air tightness between each sensor and the detector tube. A few millimeters of the sensor top for air inlet is located inside of the tube for better uptake of important gases (VOCs). Corresponding sensors are placed in corresponding, numbered locations on each side of the square cross section tube, 4×8 sensors for a total of 32 sensors (Table 3). The detector tube is extended forward with a upside down "T" shaped tube (FIG. 1). The two pipes of the entire air inlet (vertical shaft and horizontal shaft; T-shaped) have the same diameter (2 cm) and length (11 cm), each with a volume of 138 $cm^3$.

The vertical shaft of the air inlet is provided with an air filter with activated coal (Sundström, Sweden) to minimize or eliminate the influence of examination room contaminants on signals during the first 360 seconds, i.e. sensors' active time of measurement. With the sample holder in place, air flow emanating from the vertical shaft is transported to the horizontal shaft of the air inlet, the latter shaft being partly closed off by the sample holder. In the horizontal shaft with the sample holder present, the tube diameter of the air intake is cut in half. This causes the air to move faster over the sample and increases the concentration of VOCs in the detector tube. The detector tube with sensors has a considerably larger diameter than the air inlet, which leads to a slower flow of air, thus giving better ability for the sensors to detect entrapped VOCs. The horizontal tube is provided for placement of the sample holder (FIG. 2). After removal of the sample holder with the sample (after the 360th second of the total of 600 seconds' analysis time), the air goes through the horizontal tube, with the flow of air having a higher speed. A system with two separate air inlets shortens and improves the sensor recovery time. Using a horizontal tube without the resistance of an air filter mounted on the vertical tube improves the second part of the analysis by increasing the airflow through the detector tube. This means that the sensors are cleared faster and regain original resistance more rapidly before the next analysis, whereby the unit becomes more efficient. A rear tube extends the square head tube backwards. At the end of the rear tube a fan is fitted (Micro Nell Ltd., Switzerland) to draw air through the detector tube provided with sensors. This rear tube fitted with a fan may have the same diameter, length and volume as each of the two shafts of the air inlets. The fan has a separate power supply. The voltage used for the fan was chosen based on the air resistance from the air filter used.

The sample holder has been custom made to fit exactly in the horizontal air inlet part, and has been designed to ensure that a sufficiently large surface of e.g. blood plasma (or other sample, e.g. a liquid sample) can form, for sufficient emission of VOCs (FIG. 2). The sample holder dimensions are: 60 mm in length, 11 mm in width and 8 mm in depth. The surface of the liquid sample surface is 6.6 $cm^2$.

Sensor selection was based on results from previous investigations carried out with gas chromatography. The results showed that predominantly hydrocarbons dominate the VOC of ovarian cancer (Table 2). Aromatic hydrocarbons and other hydrocarbons may be derived from dead cells in the tumor mass. Up to 90% of the cancer tumor mass may consist of dead or dying cells. Thus, these substances are present in much higher concentrations in the blood of cancer patients than they are in blood of healthy people. TGS metal oxide sensors ($SnO_2$) from Figaro Engineering Inc., Japan, were chosen. These sensors can detect both aromatic and other hydrocarbons with good results. Moreover, they are relatively inexpensive and have a long lifetime.

TABLE 2

| |
|---|
| 1, Triethylamine |
| 2, Pyridine |
| 3, Toluene |
| 4, p-Xylene |
| 5, E,Z-8,10-Dodecadien-1-ol * |
| 6, Trifluoromethylbenzene |
| 7, Hexadeconic acid |
| 8, Docosane |
| 9, 3-Methylhexadecane |
| 10, Tetracosane |
| 11, Heptadecane |

Eight different sensors were mounted on each side of the detector tube, sensor positions called 1-8 (Table 3). In each position an identical sensor is placed in each detector tube wall, giving a total of 32 sensors in the sensor tube (FIG. 1). Since each sensor has a different heating voltage, and thus working at a different temperature from its peers, the signals from each sensor in a sensor quadruple set varies. The temperature differences enable four identical sensors to detect far more substances than four identical sensors working at the same temperature may.

TABLE 3

| Position/sensor name |
|---|
| 1, TGS 2602 |
| 2, TGS 2603 |
| 3, TGS 2620 |
| 4, TGS 2611-E00 |
| 5, TGS 2600 |
| 6, TGS 2611 -C00 |
| 7, TGS 2444 |
| 8, TGS 2610 |

For detection of ovarian carcinoma sensors No. 1, 2, 3 and 5 are of great importance but also sensors No 4 and 7 provide important contributions to the diagnosis. The other two sensors are potentially important in the diagnosis of other carcinomas such as gynecological cancers, except for ovarian carcinomas.

Each group of eight sensors placed on the same side of the detector tube is controlled by a separate circuit card, making a total of four identical cards used in the device. On each circuit card is mounted a potentiometer to the heater voltage circuit of each sensor, to be able to individually set the optimal temperature for maximum sensor sensitivity. It was found that for detection of VOCs from ovarian cancer a voltage between 2.5V and 5.5V is required. For each group of four identical sensors, the heater voltage for each individual sensor is set so that the temperature differences between the 4 (or more) identical sensors (one on each side of the detector tube) enables the detection of a wide range of gases (Table 4).

TABLE 4

The digits represent voltage. H = heating circuit; S = sensor circuit. A, B, C and D, respectively, represent the four different sides of the sensor tube with rectangular cross section.

|   |   | TGS 2602 | TGS 2603 | TGS 2620 | TGS 2611-E00 | TGS 2620 | TGS 2611-C00 | TGS 2444 | TGS 2610 |
|---|---|------|------|------|------|------|------|------|------|
| A | H | 3.7  | 4.0  | 3.0  | 3.3  | 5.0  | 5.0  | 5.3  | 4.5  |
|   | S | 4.9  | 4.9  | 4.8  | 4.9  | 4.9  | 4.9  | 4.9  | 4.8  |
| B | H | 4.0  | 4.4  | 3.5  | 3.6  | 4.5  | 4.5  | 5.0  | 4.0  |
|   | S | 4.9  | 4.9  | 4.8  | 4.9  | 4.9  | 4.9  | 4.9  | 4.9  |
| C | H | 4.5  | 4.7  | 4.0  | 3.9  | 3.5  | 3.0  | 4.8  | 3.5  |
|   | S | 4.8  | 4.9  | 4.9  | 4.9  | 4.9  | 4.9  | 4.9  | 4.9  |
| D | H | 4.8  | 5.0  | 4.5  | 4.2  | 3.0  | 2.8  | 4.6  | 3.0  |
|   | S | 4.9  | 4.9  | 4.8  | 4.9  | 4.9  | 4.9  | 4.9  | 4.8  |

Signal output is obtained through the load resistors. Various load resistances were tested within the range of Table 2, to determine which load resistances provide the best signal quality for VOCs from plasma of patients with ovarian cancer. As to the sensor resistances, it was found that the minimum values of sensor resistance are the most suitable for ovarian cancer detection. For diagnosis of other cancers, other values of sensor resistance may be more useful. The integrated resistors are shown below (Table 5).

TABLE 5

| Position/sensor name | Load resistors |
|---|---|
| 1, TGS 2602 | 20 kOhm |
| 2, TGS 2603 | 30 kOhm |
| 3, TGS 2620 | 2 kOhm |
| 4, TGS 2611-E00 | 10 kOhm |
| 5, TGS 2600 | 24 kOhm |
| 6, TGS 2611 -C00 | 2 kOhm |
| 7, TGS 2444 | 20 kOhm |
| 8, TGS 2610 | 2 kOhm |

The analogue to digital converter used was a Measurement card by National Instruments, USB 6218 with 32 inputs, 16 bit, which was connected to each sensor separately via the control cards' circuit voltage. The digital signal was fed to a computer through a USB port A computer-based analysis unit is part of the device for cancer detection. The computer-based analysis unit comprises software and hardware. Measurement software has been developed in the development environment Labview. The purpose of the measurement software is to collect and present data from the gas sensors and to store the information in graphical and text format (in Excel). The measurement software is running on a computer that has Windows 7. The measurement program is flexible and modular. The measurement software collects 10 measured data signals per second. The files are then statistically analyzed in the computer stats program.

For the statistical analysis, the signals are divided into 5 separate time intervals. These intervals are important characteristics of the invention. By statistically comparing the relatively short time intervals of the signals, an opportunity for a more sensitive discrimination of signals arises. The following time periods were chosen and were the basis for statistical analyses: t1=0-20 s; t2=20-120 s; t3=120-200 s; t4=200-360 s; t5=360-500 s. The program calculates the maximum-minimum/minimum values in Volt for each time interval of each signal from each individual sensor. Thereupon, the data is analyzed with logistic regression using the lasso method and cross-validation. Values above 0.5 represent VOCs from ovarian cancer. Final results are displayed as a value between 0 and 1. Values above 0.5 represent VOCs from ovarian cancer.

Power supply to the device absent the computer is by way of a UNI-T DC power supply (0-32V; 0-3A). Two separate input voltages are taken from the power supply: the heating voltage is 9.0V while the sensor circuit voltage is 5.0V.

Use of a Device According to the Embodiment Described Above

The device for cancer detection needs to be "conditioned" for one hour before use, for the sensors to reach the proper operating temperature. The temperature in the examination room needs to be between 20-21 degrees and relative humidity (RH) between 25-30% for optimum results. In the sample holder's cavity, 0, 8-1 ml of plasma is placed. It is important that the plasma covers the bottom of the cavity evenly, to ensure a large and equal surface area in all measurements. The analysis process is started via the measurement program Labview, on the computer, but without the fan on. The program runs for 20 s for establishing a "base line" for each sensor signal, whereupon the sample holder with plasma in its cavity is inserted into the detector tube. The computer records the signals for a further 20 s without the fan on. After 2×20 s of measurements, the fan is switched on. Registration is made of the ascending signal curves, during 360 seconds (including the 2×20 s initial baseline measurements). Thereupon, the sample holder is removed from the detector tube and the program runs up to a total of 600 s. The latter period is the "sensor recovery" time, i.e. signals from individual sensors decrease and return to the "base line" again. New tests runs can be made immediately after the signal has reached base line.

The last test on 150 plasma samples from ovarian cancer patients and healthy controls showed 92% sensitivity and 92% specificity. This is a result that no currently available medical analysis equipment or method can even come close to.

Blood plasma from 12 endometrial, 8 vulva, and 10 cervical cancer (all gynecological cancers) patients was analyzed, and compared with blood plasma from 65 ovarian cancer patients. The device was able to distinguish, at close to 100%, ovarian cancers from the others.

GENERAL REFERENCES

1, Willis C M, et al. Olfactory detection of human bladder cancer by dogs: proof of principle study. *BMJ.* 2004; 329:712.

2, Avinash B, et al; Detection and differentiation of normal, cancerous, and metastatic cells using nanoparticle-polymer sensor arrays PNAS, 2009; 106: 27, 10912-10916

7, Buljubasic J. et al; The scent of human diseases: a review on specific volatile organic compounds as diagnostic biomarkers, Flavour and Flagrance J. 2015; 30; 5

OWN WORKS LINKED TO THE INVENTION

3, Horvath G., et al: Human Ovarian Carcinomas Detected by Specific Odor Integr. Cancer Ther. 2008; 7; 76

4, Horvath G., et al: Characteristic odor in the blood reveals ovarian carcinoma BMC Cancer 2010, 10:643

5, Horvath G., et al: Cancer odor in the blood of ovarian cancer patients: a retrospective study of detection by dogs during treatment, 3 and 6 months afterward BMC Cancer 2013, 13:396

6, Horvath G., et al: Different volatile signals emitted by human ovarian carcinoma and healthy tissues Future Oncology, 2010, 6(6)1043-1049

GENERAL REFERENCES

1, Willis C M, et al. Olfactory detection of human bladder cancer by dogs: proof of principle study. *BMJ.* 2004; 329:712.

2, Avinash B, et al; Detection and differentiation of normal, cancerous, and metastatic cells using nanoparticle-polymer sensor arrays PNAS, 2009; 106: 27, 10912-10916

7, Buljubasic J. et al; The scent of human diseases: a review on specific volatile organic compounds as diagnostic biomarkers, Flavour and Flagrance J. 2015; 30; 5

OWN WORKS LINKED TO THE INVENTION

3, Horvath G., et al: Human Ovarian Carcinomas Detected by Specific Odor Integr. Cancer Ther. 2008; 7; 76

4, Horvath G., et al: Characteristic odor in the blood reveals ovarian carcinoma BMC Cancer 2010, 10:643

5, Horvath G., et al: Cancer odor in the blood of ovarian cancer patients: a retrospective study of detection by dogs during treatment, 3 and 6 months afterward BMC Cancer 2013, 13:396

6, Horvath G., et al: Different volatile signals emitted by human ovarian carcinoma and healthy tissues Future Oncology, 2010, 6(6)1043-1049

The invention claimed is:

1. Device for cancer detection comprising:
    a sample holder for a liquid or solid body sample;
    an air inlet with a horizontal and a vertical shaft, wherein each may have the same volume;
    an air filter fitted within one of the horizontal and vertical shafts, the other of the horizontal and vertical shafts configured to hold a sample;
    a detector tube;
    at least four of each of at least four different types of metal oxide sensors, wherein the at least four of each of the at least four different types of metal oxide sensors are disposed in a common cross-sectional plane of the detector tube, and wherein one of each of the at least four different types of metal oxide sensors are distributed along a length of the detector tube and disposed through a wall of the detector tube;
    each sensor configured to be supplied with an adjustable heating voltage and an adjustable circuit voltage, and each with a set sensor resistance interval;
    an analogue to digital signal converter connected to each sensor;
    a computer-based analysis program operably connected to each individual sensor of the detector tube, through the analog to digital signal converter, for registration of signals and analysis of results; and
    an electricity source;
    wherein the device is configured to analyse the sample during a set time and to analyse the sensor values.

2. Device according to claim 1, wherein the detectors constitute $SnO_2$ sensors.

3. Device according to claim 1, wherein each of the at least four sensors of each of the at least four different types of metal oxide sensors is configured to be supplied with a different heating voltage.

4. Device according to claim 1, wherein each of the sensors has an inherent resistance and is configured in series with a load resistor having more than twice the inherent resistance of the sensor the sample holder is heated to facilitate transport of the volatile organic compounds from the sample holder to the detector tube.

5. Device according to claim 1, wherein at least an inner surface of the detector tube is made from or coated with stainless steel or teflon.

6. Device according to claim 1, wherein one of each of the at least four different types of metal oxide sensors that are distributed along a length of the detector tube are connected to and controlled by a common circuit card, and the common circuit card is connected to the analogue to digital signal converter.

7. Device according to claim 1, wherein the detector tube comprises the sensors TGS 2602, TGS 2603, TGS 2620, and TGS 2600.

8. Device according to claim 3, wherein the heating voltage to each sensor is regulated between 2.5-5.5 V.

9. Device according to claim 1, wherein the device has been provided with an additional air inlet.

10. Device according to claim 1, wherein the set time is divided into separate parts.

11. Device according to claim 1, wherein the set time is divided into 5 separate parts.

12. Method of detecting or screening for cancer through the detection of volatile organic compounds (VOCs), comprising the steps of:
    providing a device according to claim 1;
    inserting the sample holder into the device with a blood, blood plasma, cyst fluid, urine, or tumor tissue sample; and
    measuring the sample for VOCs with the device according to claim 1.

13. Method of detecting or screening for cancer according to claim 12, wherein
    the measuring step further comprises setting the heater voltage for each of the at least four of the same type of metal oxide sensors that are disposed in a common cross-sectional plane of the detector tube so that each of the at least four of the same type of metal oxide sensors has a different temperature.

14. The device as in claim 1 further comprising an individual potentiometer and load resistor with individually calculated resistance, respectively, connected to each sensor of the detector tube.

* * * * *